United States Patent
Hess et al.

(10) Patent No.: US 8,501,155 B2
(45) Date of Patent: Aug. 6, 2013

(54) BIOCHEMICAL MARKERS FOR ACUTE PULMONARY EMBOLISM

(75) Inventors: Georg Hess, Mainz (DE); Andrea Horsch, Mannheim (DE); Dietmar Zdunek, Tutzingen (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 537 days.

(21) Appl. No.: 12/631,926

(22) Filed: Dec. 7, 2009

(65) Prior Publication Data

US 2010/0203571 A1 Aug. 12, 2010

Related U.S. Application Data

(62) Division of application No. 11/849,407, filed on Sep. 4, 2007, now Pat. No. 7,651,679.

(30) Foreign Application Priority Data

Sep. 15, 2006 (EP) .................................. 06120782

(51) Int. Cl.
*A61K 49/00* (2006.01)
(52) U.S. Cl.
USPC ........................................................ 424/9.1
(58) Field of Classification Search
USPC ........................................................ 424/9.1
See application file for complete search history.

(56) References Cited

U.S. PATENT DOCUMENTS 5,744,305 A 4/1998 Fodor et al.

FOREIGN PATENT DOCUMENTS

| EP | 648228 B1 | 11/1998 |
|---|---|---|
| GB | 2403533 A | 5/2005 |
| WO | 02/083913 A1 | 10/2002 |
| WO | WO 20061087373 A1 | 8/2006 |
| WO | WO 02/089657 A2 | 9/2007 |

OTHER PUBLICATIONS

Tatamori et al. "Vasoactive peptides in a pulmonary embolism model" Surg Today, 2002, 32:707-710.*
Bonderman, D. et al., "Bosentan Therapy for Inoperable Chronic Thromboembolic Pulmonary Hypertension," Chest: 128, 4, Oct. 2005, 2599-2603.
Bonow, R. et al., "New Insights Into the Cardiac Natriuretic Peptides," Circulation, vol. 93, No. 11, Jun. 1, 1996, 1946-1950.
Karl, J. et al., "Development of a novel, N-Terminal-proBNP (NT-proBNP) assay with a low detection limit," Scand J Clin Lab Invest 1999; 59 (suppl 230) 177-181.

Kiely, D. et al., "Elevated levels of natriuretic peptides in patients with pulmonary thromboembolism," Respiratory Medicine (2005) 99, 1286-1291.
Kostrubiec, M. et al., "Biomarker-based risk assessment model in acute pulmonary embolism," European Heart Journal (2005) 26, 2166-2172.
Nolan, J. et al., "Suspension array technology: evolution of the flat-array paradigm," Trends in Biotechnology, vol. 20, No. 1, Jan. 2002, 9-12.
Pruszczyk, P. et al., "N-terminal pro-brain natriuretic peptide in patients with acute pulmonary embolism," Eur Respir J 2003: 22;4, 649-653.
Ruskoaho, H. et al., "Cardiac Hormones as Diagnostic Tools in Heart Failure<," Endocrine Reviews 24(3) 341-356 (2003).
Yeo, K. et al., "Multicenter evaluation of the Roche NT-proBNP assay and comparison to the Biosite Triage BNP assay," Clinica Chimica Acta 338 (2003) 107-115.
Dowdy, et al., Statistics for Research, John Wiley & Sons, New York 1983—Standard Textbook.
Abroug, et al., "Association of Left-Heart Dysfunction with Severe Exacerbation of Chronic Obstructive Pulmonary Disease," Am J Respir Crit Care Med., 2006, vol. 174, pp. 990-996, Jul. 13, 2006.
Giannitsis, et al., "Risk Stratification in Pulmonary Embolism Based on Boimarkers and Echocardiography," American Heart Association, Circulation 2005, 112; 1520-1522.
Goldhaber, "Pulmonary Embolism," The Lancet, vol. 363, Apr. 17, 2004, 1295-1305.
Gattinoni, et al., "Lung Recruitment in Patients with the Acute Respiratory Distress Syndrome,"N Engl J Med, 354:17, Apr. 27, 2006.
Binder et al., "N-Terminal Pro-Brain Natriuretic Peptide or Troponin Testing Followed by Echocardiography for Risk Stratification of Acute Pulmonary Embolism," American Heart Assoc Circulation 2005; 112: 1573-1579, Sep. 6, 2005.
Perrier, et al., "Multidetector-Row Computed Tomography in Suspected Pulmonary Embolism," N Engl J Med, 352:17, Apr. 28, 2005, 1760-1768.
Hull, "Diagnosing Pulmonary Embolism with Improved Certainty and Simplicity," American Medical Association, JAMA, Jan. 11, 2006; vol. 295, No. 2, 213-215.
Kucher et al., "Low Pro-Brain Natriuretic Peptide Levels Predict Benign Clinical Outcome in Acute Pulmonary Embolism," Circulation 2003, 107: 1576-1578.

* cited by examiner

*Primary Examiner* — Bin Shen
(74) *Attorney, Agent, or Firm* — Roche Diagnostics Operations, Inc.

(57) ABSTRACT

The present invention relates to a method of differentiating between a singular and a multiple lung embolism in a subject suspected to suffer from acute lung embolism comprising determining the amount of NT-proBNP in a sample of a subject suspected to suffer from acute lung embolism and comparing the amount to a reference amount. Further, the present invention also relates to a method of differentiating between acute and chronic lung embolism in a subject comprising determining the amount of NT-proANP at a first and a second time point and comparing the determined amounts with each other. The present invention also encompasses devices and kits for carrying out the aforementioned methods.

11 Claims, 1 Drawing Sheet

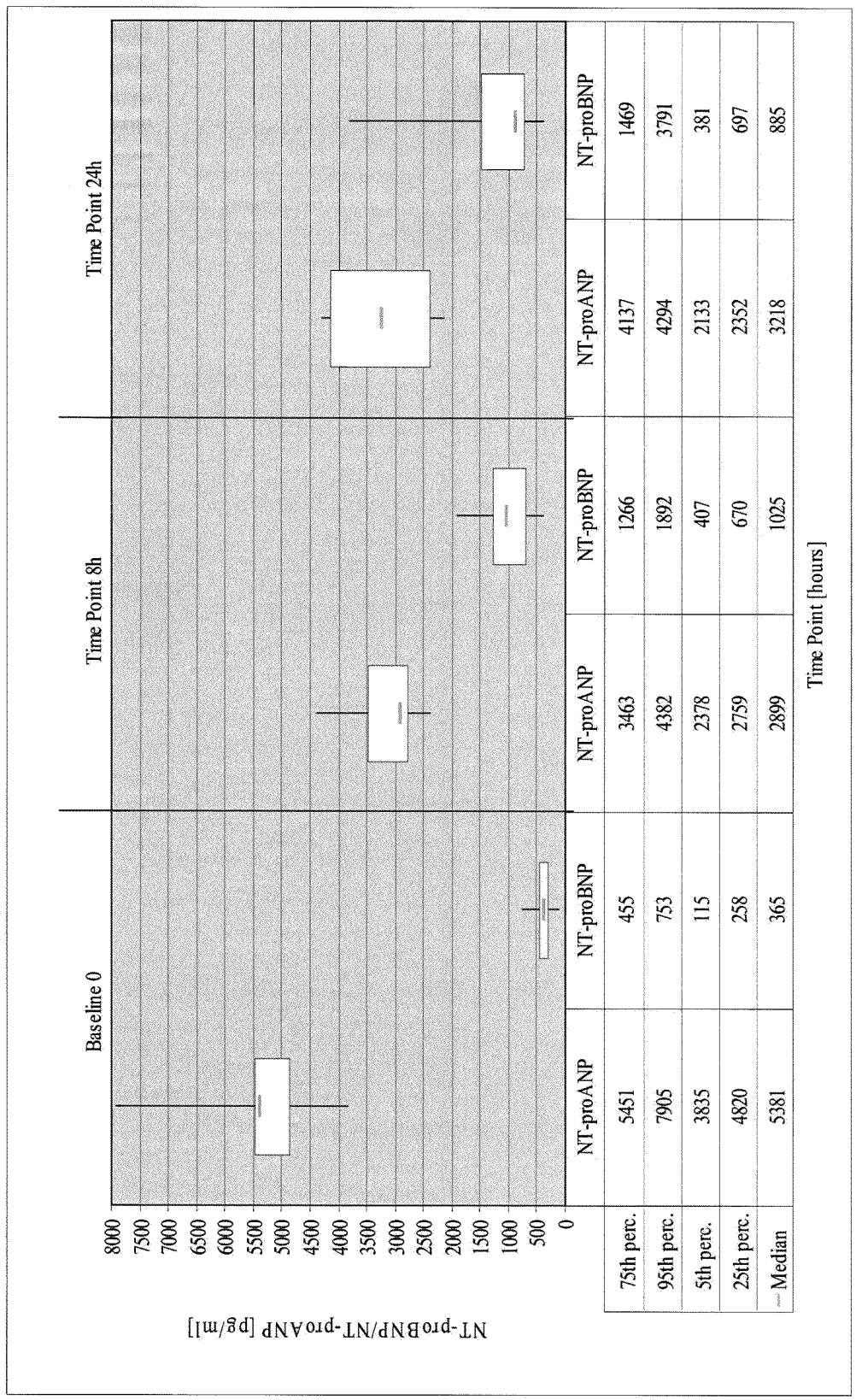

BIOCHEMICAL MARKERS FOR ACUTE PULMONARY EMBOLISM

RELATED APPLICATIONS

This application is a divisional application of U.S. Ser. No. 11/849,407 filed Sep. 4, 2007, now U.S. Pat. No. 7,651,679, which claims priority to European application EP 06120782.5 filed Sep. 15, 2006.

FIELD OF THE INVENTION

The present invention relates to a diagnostic method and, in particular, to a method of differentiating between a singular and a multiple lung embolism in a subject suspected to suffer from acute lung embolism comprising determining the amount of NT-proBNP (NT-pro brain natriuretic peptide) in a sample from a subject suspected to suffer from acute lung embolism and comparing the amount to a reference amount. Further, the present invention also relates to a method of differentiating between acute and chronic lung embolism in a subject comprising determining the amount of NT-proANP (NT-pro atrial natriuretic peptide) at a first and a second time point and comparing the determined amounts with each other. The present invention also encompasses devices and kits for carrying out the aforementioned methods.

BACKGROUND OF THE INVENTION

Lung embolism is a life threatening medical event, especially in its acute form. The characteristic clinical symptoms of acute lung embolism usually resulting in hospitalization are acute shortness of breath, collapse-like conditions, and chest pain. Lung embolism is caused by thrombosis which often occurs in femoral veins. Moreover, the thrombosis may be accompanied by further diseases such as genetically caused defects in the blood coagulation cascade or cancer diseases.

As a consequence of thrombosis, a floating thrombus may enter and occlude the lung artery. The size of the embolus determines the position of the arterial occlusion. The occlusion of a lung artery results in a right ventricular volume overload of the heart and, as a consequence thereof, often to poor support of the left heart.

Lung embolism may occur as a singular event accompanied by the aforementioned acute clinical symptoms which result, in particular in the case of emergency patients, in hospitalization, or lung embolism may be the result of multiple smaller lung emboli whereby only the most recent one is accompanied with the clinical symptoms. The latter condition is called "multiple lung embolism" hereinafter.

A reliable distinction between a singular lung embolism and a multiple based on the apparent clinical symptoms is impossible. However, the distinction as well as the reliable identification of an acute lung embolic event is, in principle, required, in order to select an appropriate therapy. For example, a singular lung embolism may be treated by thrombolytically acting drugs while an acute event as a result of a multiple lung embolism may need removal of the thrombus by surgery.

Thus, the technical problem underlying the present invention may be seen as the provision of means and methods for complying with the aforementioned needs. The technical problem is solved by the embodiments characterized in the claims and herein below.

SUMMARY OF THE INVENTION

Accordingly, the present invention relates to a method of differentiating between a singular and a multiple lung embolism in a subject suspected to suffer from acute lung, embolism comprising (a) determining the amount of NT-proBNP in a sample of a subject suspected to suffer from acute lung embolism; and (b) comparing the amount determined in step (a) to a reference amount, whereby an amount less than the reference amount is indicative for a singular lung embolism, and an amount larger than the reference amount is indicative for a multiple lung embolism.

BRIEF DESCRIPTION OF THE DRAWING

In FIG. 1, box plots are shown for the NT-proBNP and NT-proANP amounts in blood samples of patients taken at the time point of admission (0 hours, baseline), eight hours, and 24 hours after admission. Median, 95th, 75th, $25^{th}$, and 5th percentiles are also indicated. The corresponding amounts (pg/ml) are found below the box plots.

DETAILED DESCRIPTION OF THE INVENTION

The term "differentiating" as used herein means to distinguish between a subject suffering from a singular lung embolism or a multiple lung embolism whereby the subjects suffering from the diseases show essentially the same clinical symptoms, i.e. acute shortness of breath, collapse-like conditions, and/or chest pain. Moreover, the subjects may further show a right ventricular volume overload of the heart and, as a consequence thereof, often a poor support of the left heart. The term as used herein includes differentially diagnosing each condition.

Diagnosing as used herein refers to assessing the probability according to which a subject suffers from the diseases referred to in this specification. As will be understood by those skilled in the art, such an assessment is usually not intended to be correct for 100% of the subjects to be diagnosed. The term, however, requires that a statistically significant portion of subjects can be diagnosed to suffer from the disease (e.g., a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 90%, at least 95%, at least 97%, at least 98%, or at least 99%. The p-values are, preferably, 0.1, 0.05, 0.01, 0.005, or 0.0001.

Diagnosing according to the present invention also includes monitoring, confirmation, subclassification, and prediction of the relevant disease, symptoms, or risks therefor. Monitoring relates to keeping track of an already diagnosed disease or complication, e.g., to analyzing the progression of the disease or the influence of a particular treatment on the progression of disease or complication. Confirmation relates to the strengthening or substantiating a diagnosis already performed using other indicators or markers. Subclassification relates to further defining a diagnosis according to different subclasses of the diagnosed disease, e.g., defining according to mild and severe forms of the disease. Prediction relates to prognosing a disease or complication before other symptoms or markers have become evident or have become significantly altered.

The term "singular lung embolism" as used herein refers to a disease or condition accompanied with the aforementioned clinical symptoms of lung embolism, i.e. acute shortness of breath, collapse-like conditions, and/or chest pain and, optionally, right ventricular volume overload of the heart which may be accompanied by a poor support of the left heart. The singular lung embolism as referred to in accordance with the present invention is the result of a singular artery occlusion.

In accordance with the present invention, the term "multiple lung embolism" refers to a disease or condition being also accompanied by the same general clinical symptoms as specified for the singular lung embolism above. However, it is caused by multiple occlusive events wherein only the most recent event is accompanied with the apparent clinical symptoms or, in other words, the previous embolic events did not yet elicit the aforementioned symptoms up to a clinically relevant degree.

The term "subject" as used herein relates to animals, preferably mammals, and, more preferably, humans. However, it is envisaged by the present invention that the subject shall, preferably, exhibit the aforementioned apparent clinical symptoms of a singular and multiple lung embolism, respectively. Determining the amount of NT-proBNP or any other polypeptide referred to herein according to the present invention relates to measuring the amount or concentration, preferably semi-quantitatively or quantitatively. Measuring can be done directly or indirectly. Direct measuring relates to measuring the amount or concentration of the polypeptide based on a signal which is obtained from the polypeptide itself, the intensity of which directly correlates with the number of molecules of the peptide present in the sample. Such a signal, sometimes referred to herein as an intensity signal, may be obtained, e.g., by measuring an intensity value of a specific physical or chemical property of the polypeptide. Indirect measuring includes measuring of a signal obtained from a secondary component (i.e., a component not being the polypeptide itself) or a biological read-out system, e.g., measurable cellular responses, ligands, labels, or enzymatic reaction products.

In accordance with the present invention, determining the amount of the polypeptide can be achieved by all known means for determining the amount of a peptide in a sample. Said means comprise immunoassay devices and methods which may utilize labeled molecules in various sandwich, competition, or other assay formats. Said assays will develop a signal which is indicative far the presence or absence of the polypeptide. Moreover, the signal strength can, preferably, be correlated directly or indirectly (e.g. reverse-proportional) to the amount of polypeptide present in a sample. Further suitable methods comprise measuring a physical or chemical property specific for the polypeptide such as its precise molecular mass or NMR spectrum. Said methods comprise, preferably, biosensors, optical devices coupled to immunoassays, biochips, analytical devices such, as mass-spectrometers, NMR analyzers, or chromatography devices. Further, methods include microplate ELISA-based methods, fully automated or robotic immunoassays (available for example on ELECSYS analyzers, Roche Diagnostics GmbH), CBA (an enzymatic cobalt binding assay, available for example on ROCHE/HITACHI analyzers, Roche Diagnostics GmbH), and latex agglutination assays (available for example on ROCHE/HITACHI analyzers).

Preferably, determining the amount of a polypeptide comprises the steps of (a) contacting a cell capable of eliciting a cellular response, the intensity of which is indicative of the amount of the peptide, with the peptide for an adequate period of time, (b) measuring the cellular response.

For measuring cellular responses, the sample or processed sample is, preferably, added to a cell culture, and an internal or external cellular response is measured. The cellular response may include the measurable expression of a reporter gene or the secretion of a substance, e.g., a peptide, polypeptide, or a small molecule. The expression or substance shall generate an intensity signal which correlates to the amount of the peptide.

Also preferably, determining the amount of the polypeptide comprises the step of measuring a specific intensity signal obtainable from the polypeptide or a pulmonary surfactant protein in the sample.

As described above, such a signal may be the signal intensity observed at an m/z variable specific for the polypeptide observed in mass spectra or an NMR spectrum specific for the polypeptide.

Further, determining the amount of a polypeptide preferably comprises the steps of (a) contacting the peptide with a specific ligand, (b) optionally removing non-bound ligand, and (c) measuring the amount of bound ligand.

The bound ligand will generate an intensity signal. Binding according to the present invention includes both covalent and non-covalent binding. A ligand according to the present invention can be any compound, e.g., a peptide, polypeptide, nucleic acid, or small molecule, binding to the polypeptide described herein. Preferred ligands include antibodies, nucleic acids, peptides, or polypeptides such as receptors for the polypeptide and fragments thereof comprising the binding domains for the peptides, and aptamers, e.g., nucleic acid or peptide aptamers. Methods to prepare such ligands are well-known in the art. For example, identification and production of suitable antibodies or aptamers is also offered by commercial suppliers. The person skilled in the art is familiar with methods to develop derivatives of such ligands with higher affinity or specificity. For example, random mutations can be introduced into the nucleic acids, peptides, or polypeptides. These derivatives can then be tested for binding according to screening procedures known in the art, e.g., phage display. Antibodies as referred to herein include both polyclonal and monoclonal antibodies as well as fragments thereof, such as Fv, Fab, and F(ab)2 fragments that are capable of binding antigen or hapten. The present invention also includes humanized hybrid antibodies wherein amino acid sequences of a non-human donor antibody exhibiting a desired antigen specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the ligand or agent binds specifically to the polypeptide. Specific binding according to the present invention means that the ligand or agent should not bind substantially to ("crossreact" with) another peptide, polypeptide, or substance present in the sample to be analyzed. Preferably, the specifically bound polypeptide should be bound with at least 3 times higher, more preferably at least 10 times higher, and even more preferably at least 50 times higher affinity than any other relevant peptide or polypeptide. Non-specific binding may be tolerable, if it can still be distinguished and measured unequivocally, e.g., according to its size on a western blot, or by its relatively higher abundance in the sample. Binding of the ligand can be measured by any method known in the art. Preferably, said method is semi-quantitative or quantitative. Suitable methods are described in the following.

First, binding of a ligand may be measured directly, e.g., by NMR, mass spectrometry or surface plasmon resonance.

Second, if the ligand also serves as a substrate of an enzymatic activity of the peptide or polypeptide of interest, an enzymatic reaction product may be measured (e.g., the amount of a protease can be measured by measuring the amount of cleaved substrate, e.g., on a western blot). Alternatively, the ligand may exhibit enzymatic properties itself, and the ligand/polypeptide complex or the ligand which was bound by the polypeptide, respectively, may be contacted with a suitable substrate allowing detection by the generation of an intensity signal. For measurement of enzymatic reaction products, preferably the amount of substrate is saturating. The substrate may also be labeled with a detectable label prior to the reaction. Preferably, the sample is contacted with the substrate for an adequate period of time. An adequate period of time refers to the time necessary for a detectable, preferably measurable, amount of product to be produced. Instead of measuring the amount of product, the time necessary for appearance of a given (e.g., detectable) amount of product can be measured.

Third, the ligand may be coupled covalently or non-covalently to a label allowing detection and measurement of the ligand. Labeling may be done by direct or indirect methods. Direct labeling involves coupling of the label directly (covalently or non-covalently) to the ligand. Indirect labeling involves binding (covalently or non-covalently) of a secondary ligand to the first ligand. The secondary ligand should specifically bind, to the first ligand. Said secondary ligand may be coupled with a suitable label and/or be the target (receptor) of tertiary ligand binding to the secondary ligand. The use of secondary, tertiary, or even higher order ligands is often used to increase the signal. Suitable secondary and higher order ligands may include antibodies, secondary antibodies, and the well-known streptavidin-biotin system (Vector Laboratories, Inc.). The ligand or substrate may also be "tagged" with one or more tags as known in the art. Such tags may then be targets for higher order ligands. Suitable tags include biotin, digoxigenin, his-tag, glutathione-S-transferase, FLAG, GFP, myc tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels (e.g., "magnetic beads," including paramagnetic and superparamagnetic labels), and fluorescent labels. Enzymatically active labels include, e.g., horseradish peroxidase, alkaline phosphatase, beta-galactosidase, luciferase, and derivatives thereof. Suitable substrates for detection include di-amino-benzidine (DAB), 3,3'-5,5'-tetramethyl-benzidine, NBT-BCIP (4-nitro blue tetrazolium chloride and 5-bromo-4-chloro-3-indolyl-phosphate, available as ready-made stock solution from Roche Diagnostics GmbH), CDP-Star (Amersham Biosciences), and ECF (Amersham Biosciences). A suitable enzyme-substrate combination may result in a colored reaction product, fluorescence, or chemiluminescence, which can be measured according to methods known in the art (e.g., using a light-sensitive film or a suitable camera system). As for measuring the enzymatic reaction, the criteria given above apply analogously. Typical fluorescent labels include fluorescent proteins (such as GFP and its derivatives), Cy3, Cy5, Texas Red, fluorescein, and the Alexa dyes (e.g., Alexa 568). Further fluorescent labels are available, e.g., from Molecular Probes (Oregon). Also the use of quantum dots as fluorescent labels is contemplated. Typical radioactive labels include 35S, 125I, 32P, 33P, and the like. A radioactive label can be detected by any method known and appropriate, e.g., a light-sensitive film or a phosphor imager. Suitable measurement methods according the present invention also include precipitation (particularly immunoprecipitation), electrochemiluminescence (electro-generated chemiluminescence), RIA (radioimmunoassay), ELISA (enzyme-linked immunosorbent assay), sandwich enzyme immune tests, electrochemiluminescence sandwich immunoassays (ECLIA), dissociation-enhanced lanthanide fluoroimmunoassay (DELFIA), scintillation proximity assay (SPA), turbidimetry, nephelometry, latex-enhanced turbidimetry or nephelometry, or solid phase immune tests. Further methods known in the art (such as gel electrophoresis, 2D gel electrophoresis, SDS polyacrylamide gel electrophoresis (SDS-PAGE), western blotting, and mass spectrometry) can be used alone or in combination with labeling or other detection methods as described above.

Furthermore preferably, determining the amount of a polypeptide comprises (a) contacting a solid support comprising a ligand for the polypeptide as specified above with a sample comprising the polypeptide and (b) measuring the amount of the polypeptide which is bound to the support.

The ligand, preferably chosen from the group consisting of nucleic acids, peptides, polypeptides, antibodies, and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes, etc. The ligand or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said ligand are well known and include, but are not limited to ionic, hydrophobic, covalent interactions, and the like. It is also contemplated to use "suspension arrays" as arrays according to the present invention (Nolan J P, Sklar L A. (2002). Suspension array technology: evolution of the flat-array paradigm. Trends Biotechnol. 20(1):9-12). In such suspension arrays, the carrier, e.g. a microbead or microsphere, is present in suspension. The array consists of different microbeads or microspheres, possibly labeled, carrying different ligands. Methods of producing such arrays, for example based on solid-phase chemistry and photo-labile protective groups, are generally known (U.S. Pat. No. 5,744, 305).

The term "amount" as used herein encompasses the absolute amount of the NT-proBNP or any other polypeptide referred to herein, the relative amount or concentration of the NT-proBNP or any other polypeptide referred to herein, as well as any value or parameter which correlates thereto. Such values or parameters comprise intensity signal values from all specific physical or chemical properties obtained from the polypeptide referred to herein by direct measurements, e.g., intensity values in mass spectra or NMR spectra. Moreover, encompassed are all values or parameters which are obtained by indirect measurements specified elsewhere in this description, e.g., expression levels determined from biological read-out systems in response to the polypeptide or any other polypeptide referred to herein or intensity signals obtained from specifically bound ligands. It is to be understood that values correlating to the aforementioned amounts or parameters can also be obtained by all standard mathematical operations.

The term "NT-proBNP" relates to a polypeptide comprising, preferably, 76 amino acids in length corresponding to the N-terminal portion of the human NT-proBNP molecule. The structure of the human BNP and NT-proBNP has been described already in detail in the prior art, e.g., WO 02/089657, WO 02/083913, and Bonow 1996, New Insights into the cardiac natriuretic peptides, Circulation 93: 1946-1950. Preferably, human NT-proBNP as used herein is human NT-proBNP as disclosed in EP 0 648 228 B1 or under GeneBank accession number NP-002512.1; GI:4505433. These prior art documents are incorporated herein by reference with respect to the specific sequences of NT-proBNP and variants thereof disclosed therein.

The NT-proBNP referred to in accordance with the present invention further encompasses allelic and other variants of said specific sequence for human NT-proBNP discussed above. Specifically envisaged are variant polypeptides which are on the amino acid level at least 60% identical, more preferably at least 70%, at least 80%, at least 90%, at least 95%, at least 98% or at least 99% identical to human NT-proBNP. Substantially similar and also envisaged are proteolytic degradation products which are still recognized by the diagnostic means or by ligands directed against the respective full-length peptide. Also encompassed are variant polypeptides having amino acid deletions, substitutions, and/or additions compared to the amino acid sequence of human NT-proBNP as long as the polypeptides have NT-proBNP properties. NT-proBNP properties as referred to herein are the essential immunological and/or biological properties. Preferably, the NT-proBNP variants have immunological properties (i.e., epitope composition) comparable to those of NT-proBNP. Thus, the variants shall be recognizable by the aforementioned means or ligands used for determination of the amount of the specific human NT-proBNP sequences referred to above. Biological and/or immunological NT-proBNP properties can be detected by the assay described in Karl et al. (Karl 1999, Development of a novel, N-Terminal-proBNP (NT-proBNP) assay with a low detection limit, Scand J Clin Invest 59:177-181) and Yeo et al. (Yeo 2003, Multicenter evaluation of the Roche NT-proBNP assay and comparison to the Biosite Triage assay, Clinica Chimica Acta 338:107-115). Variants also include posttranslationally modified NT-proBNPs such as glycosylated, myristylated, or phosphorylated variants.

A variant in accordance with the present invention is also a peptide or polypeptide which has been modified after collection of the sample, for example, by covalent or non-covalent attachment of a label, particularly a radioactive or fluorescent label, to the peptide.

The term "sample" refers to a sample of a body fluid, to a sample of separated cells, or to a sample from a tissue or an organ. Samples of body fluids can be obtained by well known techniques and include, preferably, samples of blood, plasma, serum, or urine. Tissue or organ samples may be obtained from any tissue or organ by, e.g., biopsy. Separated cells may be obtained from the body fluids or the tissues or organs by separating techniques such as centrifugation or cell sorting.

"Comparing" as used herein encompasses comparing the amount of the NT-proBNP or any other polypeptide referred to herein comprised by the sample to be analyzed with an amount of a suitable reference source specified below in this description. It is to be understood that comparing as used herein refers to a comparison of corresponding parameters or values, e.g., an absolute amount is compared to an absolute reference amount, while a concentration is compared to a reference concentration, or an intensity signal obtained from a test sample is compared to the same type of intensity signal from a reference sample. The comparison referred to in step (b) of the method of the present invention may be carried out manually or computer assisted. For a computer assisted comparison, the value of the determined amount may be compared to values corresponding to suitable references which are stored in a database by a computer program. The computer program may further evaluate the result of the comparison, i.e., automatically providing a differential diagnosis for the diseases referred to herein in a suitable output format.

The term "reference amount" as used herein refers to an amount which allows assessing whether a subject suffers from any one of the aforementioned diseases or disorders by a comparison as referred to above. Accordingly, the reference may either be derived from a subject known to suffer from singular lung embolism or multiple lung embolism. It is to be understood that if a reference from a subject is used which suffers from singular lung embolism, an amount NT-proBNP in a sample of a test subject being essentially identical to said reference amount shall be indicative for a singular lung embolism. Likewise, if a reference from a subject known to suffer from multiple lung embolism is used, an amount of NT-proBNP in a sample of a test subject being essentially identical to said reference amount shall be indicative for a multiple lung embolism. The reference amount applicable for an individual subject may vary depending on various physiological parameters such as age, gender, or subpopulation. Thus, a suitable reference amount may be determined by the method of the present invention from a reference sample to be analyzed together, i.e., simultaneously or subsequently, with the test sample. It has been found that an amount of NT-proBNP larger than a threshold (i.e., a reference amount) being 6 to 12 times the upper limit of normal (ULN), is indicative for a multiple lung embolism. An amount below the threshold is indicative for a singular lung embolism. Preferably, the ULN is 80 to 150 pg/ml and, more preferably, 125 pg/ml. More preferably, the reference amount is 1000 pg/ml. It is to be understood that the aforementioned amounts may vary due to statistics and errors of measurement.

Advantageously, it has been found that the amount of NT-pro BNP present in a sample of a subject showing the apparent clinical symptoms of an acute lung embolic event allows for a differential diagnosis with respect to the cause of the symptoms, i.e., it can be diagnosed whether the lung embolism is a singular or multiple lung embolism. Thanks to the present invention, subjects and, in particular, emergency patients can be more readily and reliably diagnosed and subsequently treated according to the result of the differential diagnosis.

The explanations and definitions of the terms made above and herein below apply accordingly for all embodiments characterized in this specification and the claims.

The following embodiments are particularly preferred embodiments of the method of the present invention.

In a preferred embodiment of the method of the present invention, said reference amount is between 6 and 12 times the upper limit of normal (ULN) for NT-proBNP. More preferably, the ULN is 125 pg/ml.

In a furthermore preferred embodiment of the method of the present invention, said reference amount is 1000 pg/ml.

In a preferred embodiment of the method of the present invention, the method further comprises the steps of (c) determining the amount of NT-proANP in the sample simultaneously to the amount of NT-proBNP in step (a); (d) determining the amount of NT-proANP in a further sample of the subject wherein said further sample is from a time point after a period of time; and (e) comparing the amount of NT-proANP determined in step (d) to the amount of NT-proANP determined in step (c), wherein a decrease in NT-proANP is indicative for acute lung embolism.

Under "simultaneously" as used herein is to be understood that the amount of NT-proANP is to be determined at the same time as the amount of NT-proBNP. The NT-proANP amount may be determined for the same sample as the NT-proBNP amount. Alternatively, it may be determined in a different sample. However, the different sample shall be obtained from the same subject at the same time as the sample to be used for NT-proBNP determination.

The term "NT-proANP" as used in accordance with the present invention has an amino acid sequence of 98 amino acids in length corresponding to the N-terminal portion of the human NT-proANP molecule. The structure of the human ANP and NT-proANP has been described already in detail in the prior art, e.g., Bonow, 1996, New insights into the cardiac natriuretic peptides, Circulation 93: 1946-1950. Preferably, human NT-proANP as used herein is human NT-proANP as disclosed in GeneBank accession number NP-006163.1; GI:23510319. These prior art documents are incorporated herein by reference with respect to the specific sequences of NT-proANP and variants thereof disclosed therein.

The NT-proANP referred to in accordance with the present invention further encompasses allelic and other variants of said specific sequence for human NT-proANP discussed above. Specifically envisaged are variant polypeptides which are on the amino acid level at least 60% identical, more preferably at least 70%, at least 80%, at least 90%, at least 95%, at least 98% or at least 99% identical to human NT-proANP. Substantially similar and also envisaged are proteolytic degradation products which are still recognized by the diagnostic means or by ligands directed against the respective full-length peptide. Also encompassed are variant polypeptides having amino acid deletions, substitutions, and/or additions compared to the amino acid sequence of human NT-proANP as long as the polypeptides have NT-proANP properties. NT-proANP properties as referred to herein are the essential immunological and/or biological properties. Preferably, the NT-proANP variants have immunological properties (i.e., epitope composition) comparable to those of NT-proANP. Thus, the variants shall be recognizable by the aforementioned means or ligands used for determination of the amount of the aforementioned specific human NT-proANP sequences. Biological and/or immunological. NT-proANP properties can be detected by the assay described in Ruskoaho (2003), Endocrine Reviews 24(3):341-356. Variants also include posttranslationally modified NT-proANPs such as glycosylated, myristylated, or phosphorylated variants.

A variant in accordance with the present invention is also a peptide or polypeptide which has been modified after collection of the sample, for example, by covalent or non-covalent attachment of a label, particularly a radioactive or fluorescent label, to the peptide.

According to the preferred method referred to above, a further sample is to be provided from the subject wherein said further sample has been obtained from the subject at a time point after a period of time. The period of time shall be of sufficient length to allow degradation of NT-proANP which was provided in excess as a response to the acute lung embolic event. Preferably, the time period is at least 2 hours, 4 hours, 5 hours, 6 hours, 7 hours, 8 hours, 9 hours, 10 hours, 11 hours, or 12 hours.

The term "decrease" as used herein refers to a significant decrease of the amount of NT-proANP between the samples to be compared. Whether a decrease in the amount is significant can be determined by the statistical techniques referred to elsewhere in this specification. Preferably, a decrease as used herein is a decrease in the amount of at least 10%, at least 15%, at least 20%, at least 25%, at least 30%, at least 35%, at least 40%, at least 45%, or at least 50%.

It has been found in the studies underlying the present invention that a significant decrease in the amount of NT-proANP in the blood of a subject after an acute lung embolic event is indicative for acute lung embolism. If the amount of NT-proANP, however, increases or remains at about the same level (i.e., no significant decrease occurs), the lung embolism shall be deemed not acute and thus shall be deemed chronic. It is to be understood that the present invention also relates, in principle, to the use of NT-proANP and NT-proBNP or means for the determination of NT-proANP and means for the determination of NT-proBNP for the manufacture of a diagnostic composition for differentiating between acute or chronic lung embolism. The diagnostic compositions or means shall be useful for carrying out the methods referred to in accordance with the present invention.

It follows from the above that the present invention also encompasses a method of differentiating between acute and chronic lung embolism in a subject comprising (a) determining the amount of NT-proANP in a sample of a subject suffering from lung embolism of a first time point; (b) determining the amount of NT-proANP in a sample of a subject suffering from lung embolism of a second time point after a time period; and (c) comparing the amount of NT-proANP determined in step a) to the amount of NT-proANP determined in step (b), wherein a decrease in NT-proANP is indicative for an acute lung embolism. Preferably, the time period is at least 2 hours, 4 hours, 5 hours, 6 hours, 7 hours, 8 hours, 9 hours, 10 hours, 11 hours, or 12 hours.

In a preferred embodiment of the method of the present invention, said method further comprises simultaneously determining the amount of NT-proBNP in step (a) and (b) together with the amount of NT-proANP and comparing the amounts of NT-proBNP in step (a) with the amount of NT-proBNP determined in step (b), wherein an increase in NT-proBNP is further indicative for acute lung embolism.

Specifically, it has been found that an acute embolic event can be further confirmed on the biochemical level by an increase in the amount of NT-proBNP determined after a time period referred to above. Thus, while the amount of NT-proANP over said time period is decreasing in subjects suffering from an acute lung embolism, the NT-proBNP amount will increase.

Further, the present invention relates to a method for selecting a suitable therapy for lung embolism comprising the steps of the method of the present invention and the further step of selecting a suitable therapy based on the diagnosis obtained by the aforementioned method.

As discussed above, the therapeutic interventions which are necessary differ for acute versus chronic lung embolism as well as for a singular or multiple lung embolism. Specifically, if the diagnosis is singular and/or acute lung embolism, lysis of the thrombus by thrombolytically acting drugs is a suitable therapy. Removal of the thrombus by surgery is the preferred therapy for multiple lung embolism. Thrombolytically acting drugs which may be suitable in a therapy referred to above are, preferably, recombinant tissue plasminogen activator (rtPA).

Thanks to the present invention, it can be readily distinguished between acute versus chronic and singular versus multiple lung embolism. Thereby, a suitable therapy can be immediately provided which, in particular in the case of emergency patients, shall significantly reduce the mortality rate due to lung embolism.

The present invention also pertains to a device adapted for carrying out the method of the present invention comprising (a) means for determining the amount of NT-proANP; (b) means for determining the amount of NT-proBNP; and/or (c) means for comparing the amounts of NT-proANP and NT-proBNP.

The term "device" as used herein relates to a system of means comprising at least the aforementioned means operatively linked to each other as to allow the prediction. Preferred means for determining the amount of the polypeptides and means for carrying out the comparison are disclosed above in connection with the method of the invention. How to link the means in an operating manner will depend on the type of means included into the device. For example, where means for automatically determining the amount of the peptides are applied, the data obtained by said automatically operating means can be processed by, e.g., a computer program in order to diagnose or distinguish between the diseases referred to herein. Preferably, the means are comprised by a single device in such a case. Said device may accordingly include an analyzing unit for the measurement of the amount of the peptides in a sample and a computer unit for processing the resulting data for the differential diagnosis. Alternatively, where means such as test strips are used for determining the amount of the peptides, the means for diagnosing may comprise control strips or tables allocating the determined amount to an amount known to be accompanied with (i) an acute or a chronic lung embolism and (ii) a singular or a multiple lung embolism. The test strips are, preferably, coupled to a ligand which specifically binds to the natriuretic peptide or pulmonary surfactant protein. The strip or device, preferably, comprises means for detection of the binding of said peptides to the ligand. Preferred means for detection are disclosed in connection with embodiments relating to the method of the invention above. In such a case, the means are operatively linked in that the user of the system brings together the result of the determination of the amount and the diagnostic value thereof due to the instructions and interpretations given in a manual. The means may appear as separate devices in such an embodiment and are preferably packaged together as a kit. The person skilled in the art will realize how to link the means without further ado. Preferred devices are those which can be applied without the particular knowledge of a specialized clinician, e.g., test strips or electronic devices which merely require loading with a sample. The results may be given as output of parametric diagnostic raw data, preferably as absolute or relative amounts. It is to be understood that these data will need interpretation by the clinician. However, also envisaged are expert system devices wherein the output comprises processed diagnostic raw data, the interpretation of which does not require a specialized clinician. Further preferred devices comprise the analyzing units/devices (e.g., biosensors, arrays, solid supports coupled to ligands specifically recognizing the polypeptides, plasmon surface resonance devices, NMR spectrometers, mass spectrometers, etc.) or evaluation units/devices referred to above in accordance with the method of the invention.

Under "adapted for carrying out", it shall be understood that the device is capable of automatically carrying out the methods referred to above. For such an adaptation, it is envisaged that the device comprises implemented rules for making a comparison between the determined amount of NT-proBNP and a reference amount which may be also determined by the device from a reference sample or which may virtually exist as a stored value. Moreover, the device may comprise implemented rules for determining a significant decrease in the amount of NT-proANP between two at least different samples (i.e., the samples of a first and a second time point). The implementation of such rules in the device is, preferably, accomplished by an algorithm provided in the form a storable program code run on a computer or data processing unit.

Finally, the present invention relates to a kit for carrying out the method of the present invention comprising (a) means for determining the amount of NT-proANP; (b) means for determining the amount of NT-proBNP; (c) means for comparing the amounts of NT-proANP and NT-proBNP; and (d) instructions for carrying out the aforementioned methods.

The term "kit" as used herein refers to a collection of the aforementioned means, preferably provided separately or within a single container. The container, also preferably, comprises instructions for carrying out the method of the present invention. The invention thus relates to a kit comprising a means or an agent for measuring a BNP-type peptide (i.e., NT-proANP or NT-proBNP). Such means or agent may be any suitable means or agent known to the person skilled in the art. Examples for such means or agents as well as methods for their use have been given in this specification. For example, a suitable agent may be any kind of ligand or antibody capable of specifically binding to a polypeptide referred to herein above. The kit may also comprise any other components deemed appropriate in the context of determining the amount(s) of the respective biomarkers, such as suitable buffers, filters, etc. Preferably, the kit may additionally comprise instructions, e.g., a user's manual for interpreting the results of any determination(s) with respect to the diagnoses provided by the methods of the present invention. Particularly, such manual may include information for allocating the amounts of the determined polypeptides to the kind of diagnosis, i.e., to a singular or multiple lung embolism or to an acute or chronic lung embolism. Details are to be found elsewhere in this specification. Additionally, such user's manual may provide instructions about correctly using the components of the kit for determining the amount(s) of the respective biomarker. A user's manual may be provided in paper or electronic form, e.g., stored on CD or CD ROM. The present invention also relates to the use of said kit in any of the methods according to the present invention.

All references cited in this specification are incorporated herein by reference with respect to their entire disclosure content and the disclosure content specifically mentioned in this specification.

SPECIFIC EMBODIMENTS

The following examples merely illustrate the invention. It shall, whatsoever, not be construed as to limit the scope of the invention.

Determination of NT-proBNP and NT-proANP Levels in Patients Exhibiting Acute Lung Embolism A total of 34 patients with suspected pulmonary embolism were included into the study. All patients received a CT scan within 4 hours after presentation to the emergency room.

On CT scan patients with acute but not previous pulmonary embolism (i.e., singular lung embolism) on CT scan were found in Group 1 and Group 2 (see Table 1). In Group 3 patients multiple lung embolisms by CT scan including in pulmonary arteries disease of different sizes (see Table 1). Group 1 and Group 2 differ from those assigned to Group 3 in that they have NT-proBNP levels below 1000 pg/ml.

In Group 1, a decrease in NT-proANP values of more than 10% was associated with a significant increase of NT-proBNP levels. In Group 2, an increase of NT-proANP was associated with an increase of NT-proBNP levels.

Therefore in Group 1 patients had an acute pulmonary embolism as indicated by decrease of NT-proANP followed by a significant increase in NT-proBNP which was in accordance with the result of the CT scan. In Group 2, NT-proANP and NT-proBNP levels increased, indicating a protracted course of pulmonary embolism which was again consistent with the CT result. Group 2 patients did not improve with regard to symptoms.

Patients in Group 3 showed variable responses. Protracted pulmonary embolism was seen in five patients, which was associated with an increase of NT-proANP and NT-proBNP levels. In 10 patients, the acute event could not be verified. Previous pulmonary embolisms were diagnosed by CT scan. This was associated with only miner changes in NT-proANP and NT-proBNP levels.

Decrease of NT-proANP was noted in 11 patients. In this group of patients, variable responses were recognized which included a minor acute pulmonary event as well as resolution of the disease under heparin therapy.

In the present study, the NT-proBNP and NT-proANP levels were measured in blood samples. For determination of NT-proBNP, the ELECSYS test (Roche Diagnostics, Germany) was used. NT-proANP levels were determined using the proANP ELISA (Biomedica, Austria).

The results of the study are also shown in the following tables.

TABLE 1

Baseline (0 hours) biochemical parameters of the patients admitted to the study and distribution into the three groups referred to above

| Patient | Time Point | TnT | CK-MB | Myo | NT-proBNP | NT-proANP |
|---|---|---|---|---|---|---|
| Group 1 (N = 6) | | | | | | |
| 16 | 0 | 0.208 | 2.510 | 35.01 | 163.3 | 4311.92 |
| 22 | 0 | 0.285 | 4.780 | 69.84 | 973.3 | 5328.56 |
| 27 | 0 | 0.206 | 5.42 | 154.1 | 352.7 | 5433.7 |
| 37 | 0 | 0.160 | 6.360 | 265.90 | 66.6 | 5468.78 |
| 40 | 0 | 0.082 | 5.77 | 47.76 | 376.8 | 3358.4 |
| 45 | 0 | 0.087 | 2.010 | 122.90 | 533.4 | 10341.61 |
| Median | | | | | 364.8 | 5381.1 |
| Max | | | | | 973.3 | 10341.6 |
| 75th | | | | | 533.4 | 5468.8 |
| 25th | | | | | 163.3 | 4311.9 |
| Min | | | | | 66.6 | 3358.4 |

TABLE 1-continued

Baseline (0 hours) biochemical parameters of the patients admitted to the study and distribution into the three groups referred to above

| Patient | Time Point | TnT | CK-MB | Myo | NT-proBNP | NT-proANP |
|---|---|---|---|---|---|---|
| Group 2 (N = 6) | | | | | | |
| 7 | 0 | 0.227 | 6.18 | 59.02 | 465.8 | 1794.9 |
| 28 | 0 | <0.010 | 1.400 | 36.21 | 128.30 | 1528.45 |
| 6 | 0 | 0.012 | 6.58 | 872.1 | 867.5 | 17808.6 |
| 11 | 0 | 0.455 | 6.53 | 419.6 | 479.8 | 12900.7 |
| 17 | 0 | 0.01 | 2.43 | 383.9 | 160.7 | 21314.2 |
| 32 | 0 | <0.010 | 1.090 | <21.00 | 341.40 | 3786.08 |
| Median | | | | | 341.4 | 15354.7 |
| Max | | | | | 867.5 | 21314.2 |
| 75th | | | | | 479.8 | 17808.6 |
| 25th | | | | | 341.4 | 12900.7 |
| Min | | | | | 160.7 | 3786.1 |
| Group 3 (N = 22) | | | | | | |
| 2 | 0 | 0.011 | 2.500 | 46.33 | 6653.0 | 6275.08 |
| 4 | 0 | 0.170 | 3.760 | 91.58 | 5568.0 | 3393.45 |
| 8 | 0 | 0.036 | 1.960 | 35.42 | 5912.00 | 3221.67 |
| 14 | 0 | 0.021 | 4.110 | 91.91 | 23999.0 | 11218.02 |
| 15 | 0 | 0.114 | 3.910 | 45.96 | 1472.0 | 2801.00 |
| 19 | 0 | 0.010 | 0.937 | 27.53 | 5210.00 | 2871.11 |
| 20 | 0 | 0.440 | 10.440 | 67.77 | 12450.0 | 12409.93 |
| 10 | 0 | 0.054 | 2.640 | 41.23 | 3377.0 | 3751.02 |
| 1 | 0 | 0.219 | 3.950 | 49.48 | 1623.00 | 6520.47 |
| 13 | 0 | 0.077 | 3.620 | 66.89 | 4740.00 | 4697.54 |
| 21 | 0 | 0.010 | 1.590 | 38.33 | 15522.00 | 13707.01 |
| 24 | 0 | 3.300 | 68.780 | 396.700 | 16032.00 | 13847.24 |
| 25 | 0 | <0.010 | 0.610 | 34.15 | 2162.00 | 10516.89 |
| 29 | 0 | <0.010 | 2.320 | 39.78 | 1059.00 | 3610.80 |
| 30 | 0 | <0.010 | 0.998 | 24.93 | 12478.0 | 7887.67 |
| 33 | 0 | 0.161 | 9.000 | 132.40 | 4990.0 | 8378.46 |
| 34 | 0 | 0.088 | 3.910 | 50.09 | 8287.00 | 4662.49 |
| 38 | 0 | 0.023 | 2.560 | 58.49 | 4674.0 | 4662.49 |
| 39 | 0 | 0.042 | 6.970 | 82.79 | 3526.00 | 4907.88 |
| 41 | 0 | 0.031 | 3.300 | 79.81 | 5816.00 | 11042.73 |
| 42 | 0 | 0.151 | 2.580 | 35.08 | 5538.00 | 9114.64 |
| 43 | 0 | <0.010 | 1.240 | 27.34 | 1292.00 | 1914.07 |
| Median | | | | | 5374.0 | 5591.5 |
| 95th | | | | | 16032.00 | 13707.01 |
| 75th | | | | | 8287.00 | 10516.89 |
| 25th | | | | | 2162.00 | 3393.45 |
| 5th | | | | | 1059.00 | 1914.07 |

TABLE 2

Changes of NT-proBNP in Group 3 for patients with increased, unchanged, and decreased NT-proANP levels

| | Group 3 | | |
|---|---|---|---|
| | Δ NT-proBNP [%] Mean NT-proBNP | Δ NT-proBNP [%] Mean NT-proBNP | Δ NT-proBNP [%] Mean NT-proBNP |
| Time Point | 0 (baseline) | 8 h | 24 h |
| NT-proANP, Mean | 8145.8 pg/ml | 6276.8 pg/ml | 6875.9 pg/ml |
| Increase >10%; | Δ 0% | Δ − 38% | Δ + 82%: |
| N = 6 (23%) | 5987.6 pg/ml | 3696.0 pg/ml | 10877 pg/ml |
| Δ + 10%: | Δ 0% | Δ + 273% | Δ − 74% |
| N = 6 (23%) | 1545.0 pg/ml | 5770.3 pg/ml | 407.0 pg/ml |
| Decrease >10%; | Δ 0% | Δ − 54% | Δ − 8% |
| N = 14 (54%) | 4117.1 pg/ml | 1877.3 pg/ml | 3796.9 pg/ml |
| Increase >20%; | Δ 0% | Δ + 16% | Δ + 314% |
| N = 5 (19%) | 3699.6 pg/ml | 4306.4 pg/ml | 11617.6 pg/ml |
| Δ + 20%; | Δ 0% | Δ − 3% | Δ − 14% |
| N = 10 (38%) | 5113.8 pg/ml | 4970.8 pg/ml | 4401.8 pg/ml |
| Decrease >20%; | Δ 0% | Δ − 35% | Δ + 24% |
| N = 11 (42%) | 2635.7 pg/ml | 1701.1 pg/ml | 3261.3 pg/ml |

Patients N = 22

TABLE 3

Changes of NT-proBNP in Group 2 for patients with increased, unchanged, and decreased NT-proANP levels

| | Group 2 | | |
|---|---|---|---|
| | Δ NT-proBNP [%] Mean NT-proBNP | Δ NT-proBNP [%] Mean NT-proBNP | Δ NT-proBNP [%] Mean NT-proBNP |
| Time Point | 0 (baseline) | 8 h | 24 h |
| NT-proANP, Mean | 14303 pg/ml | 19351 pg/ml | 19912.3 pg/ml |
| Increase >10% | Δ 0% 456.6 pg/ml | Δ + 68% 766.0 pg/ml | Δ + 969%: 4882 pg/ml |
| Δ + 10%: | 0 | 0 | 0 |
| Decrease >10%; | 0 | 0 | 0 |

Patients N = 6
ANP: Increase
BNP: Increase

TABLE 4

Changes of NT-proBNP in Group 1 for patients with increased, unchanged, and decreased NT-proANP levels

| | Group 1 | | |
|---|---|---|---|
| | Δ NT-proBNP [%] Mean NT-proBNP | Δ NT-proBNP [%] Mean NT-proBNP | Δ NT-proBNP [%] Mean NT-proBNP |
| Time Point | 0 (baseline) | 8 h | 24 h |
| NT-proANP, Mean | 6177.2 pg/ml | 3312.8 pg/ml | 3386.4 pg/ml |
| Increase >10% | 0 | 0 | 0 |
| Δ + 10% | 0 | 0 | 0 |
| Decrease >10% | Δ 0% 417.8 pg/ml | Δ + 159% 1081.0 pg/ml | Δ + 347% 1868.4 pg/ml |

Patients N = 6
ANP: Decrease
BNP: Increase

What is claimed is:

1. A method of differentiating between singular and multiple lung embolism in a human subject suspected of suffering from acute lung embolism comprising
    measuring an amount of NT-proBNP (NT-pro brain natriuretic peptide) in a sample taken from the subject at a first time point, wherein the NT-ProBNP has an amino acid sequence of 76 amino acids corresponding to the N-terminal portion of human NT-ProBNP,
    measuring an amount of NT-proANP (NT-pro atrial natriuretic peptide) in the sample taken from the subject at a first time point, wherein the NT-ProANP has an amino acid sequence of 98 amino acids corresponding to the N-terminal portion of human NT-ProANP,
    measuring an amount of NT-proANP in a sample taken from the subject at a second time point,
    comparing the amount of NT-proBNP measured to a reference amount of NT-proBNP, whereby a measured amount of NT-proBNP less than the reference amount is indicative of singular lung embolism and a measured amount of NT-proBNP larger than the reference amount is indicative of multiple lung embolism, and
    comparing the amount of NT-proANP measured in the sample taken at a first time point to the amount of NT-proANP measured in the sample taken at a second time point, wherein a decrease in NT-proANP from the first time point to the second time point is indicative of an acute lung embolism.

2. The method of claim 1 wherein the samples are selected from the group consisting of blood; serum, and plasma.

3. The method of claim 1 wherein the time period between the first and second time points is selected from the group consisting of at least 2 hours, 4 hours, 5 hours, 6 hours, 7 hours, 8 hours, 9 hours, 10 hours, 11 hours, and 12 hours.

4. The method of claim 1 wherein the reference amount of NT-proBNP is between 750 and 1500 pg/ml.

5. The method of claim 1 wherein the reference amount is 1000 pg/ml.

6. A method of differentiating between an acute and a chronic lung embolism in a human subject suffering from lung embolism comprising:
    measuring an amount of NT-proANP (NT-pro atrial natriuretic peptide) in a sample taken from the subject at a first time point, wherein the NT-ProANP has an amino acid sequence of 98 amino acids corresponding to the N-terminal portion of human NT-ProANP,
    measuring an amount of NT-proANP in a sample taken from the subject at a second time point, and
    comparing the amount of NT-proANP measured in the sample taken at a first time point to the amount of NT-proANP measured in the sample taken at a second time point, wherein a decrease in the amount of NT-proANP from the first time point to the second time point is indicative of acute lung embolism and an increase or no significant decrease in the amount of NT-proANP from the first time point to the second time point is indicative of chronic lung embolism.

7. The method of claim 6 wherein the samples are selected from the group consisting of blood, serum, and plasma.

8. The method of claim 6 wherein the time period between the first and second time points is selected from the group consisting of at least 2 hours, 4 hours, 5 hours, 6 hours, 7 hours, 8 hours, 9 hours, 10 hours, 11 hours, and 12 hours.

9. A method of differentiating between an acute and a chronic lung embolism in a human subject suffering from lung embolism comprising:
  measuring an amount of NT-proANP (NT-pro atrial natriuretic peptide) in a sample taken from the subject at a first time point, wherein the NT-ProANP has an amino acid sequence of 98 amino acids corresponding to the N-terminal portion of human NT-ProANP,
  measuring an amount of NT-proBNP (NT-pro brain natriuretic peptide) in the sample taken at a first time point, wherein the NT-ProBNP has an amino acid sequence of 76 amino acids corresponding to the N-terminal portion of human NT-ProBNP,
  measuring an amount of NT-proANP in a sample taken from the subject at a second time point,
  measuring an amount of NT-proBNP in the sample taken at a second time point,
  comparing the amount of NT-proANP measured in the sample taken at a first time point to the amount of NT-proANP measured in the sample taken at a second time point, wherein a decrease in the amount of NT-proANP from the first time point to the second time point is indicative of acute lung embolism and an increase or no significant decrease in the amount of NT-proANP from the first time point to the second time point is indicative of chronic lung embolism, and comparing the amount of NT-proBNP measured in the sample taken at a first time point to the amount of NT-proBNP measured in the sample taken at a second time point, wherein an increase in the amount of NT-proBNP from the first time point to the second time point is further indicative of acute lung embolism.

10. The method of claim 9 wherein the samples are selected from the group consisting of blood, serum, and plasma.

11. The method of claim 9 wherein the time period between the first and second time points is selected from the group consisting of at least 2 hours, 4 hours, 5 hours, 6 hours, 7 hours, 8 hours, 9 hours, 10 hours, 11 hours, and 12 hours.

* * * * *